United States Patent [19]

Fischer, deceased

[11] 3,963,475

[45] June 15, 1976

[54] HERBICIDAL MIXTURES OF 3-LOWER ALKYL-2,1,3-BENZOTHIADIAZINONE-(4)-2,2-DIOXIDES AND 3,5-DIBROMO-4-HYDROXYBENZALDOXIME-0-(NITROPHENYL)ETHERS

[75] Inventor: Adolf Fischer, deceased, late of Mutterstadt, Germany, by Caecilia Emma Fischer, legal representative

[73] Assignee: BASF Aktiengesellschaft, Ludwigshafen (Rhine), Germany

[22] Filed: Feb. 10, 1975

[21] Appl. No.: 548,388

Related U.S. Application Data

[62] Division of Ser. No. 432,676, Jan. 11, 1974, abandoned, which is a division of Ser. No. 343,629, March 22, 1973, Pat. No. 3,888,655.

[30] Foreign Application Priority Data

Apr. 13, 1972 Germany.............................. 2217722

[52] U.S. Cl........................................ 71/91; 71/121
[51] Int. Cl.$^2$............................................ A01N 9/12
[58] Field of Search................................ 71/91, 121

[56] References Cited
UNITED STATES PATENTS 3,708,277  1/1973  Zeidler et al. ........................... 71/91
3,733,359  5/1973  Hubele.................................. 71/121

OTHER PUBLICATIONS
Fischer I, "Herbicidal Compositions" (1971), CA 75, No. 110714w, (1971).

Fischer II, "Herbicidal Compositions, etc.," (1971), CA 75, No. 75217, (1971).

*Primary Examiner*—Glennon H. Hollrah
*Attorney, Agent, or Firm*—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide or a salt thereof and (b) a compound of the formula

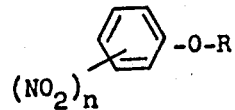

where *n* denotes one of the integers 1 and 2, and R denotes the radical

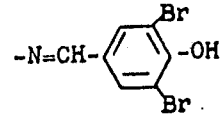

8 Claims, No Drawings

HERBICIDAL MIXTURES OF 3-LOWER ALKYL-2,1,3-BENZOTHIADIAZINONE-(4)-2,2-DIOXIDES AND 3,5-DIBROMO-4-HYDROXYBENZALDOXIME-O-(NITROPHENYL)ETHERS

RELATED APPLICATION

This application is a division of my copending application Ser. No. 432,676, filed Jan. 11, 1974, now abandoned which in turn is a division of my application Ser. No. 343,629, filed Mar. 22, 1973, now U.S. Pat. No. 3,888,655 the disclosure of which is incorporated herein by reference.

The present invention relates to herbicide comprising a composition of several active ingredients.

It is known that substituted phenyl ethers, carbamates, terephthalates, acid amides, benzoic acids, fluorenecarboxylic acids and benzothiadiazinones have a herbicidal action. However, this action is poor.

I have now found that a composition of
a. a compound of the formula

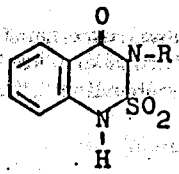

where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and b. a compound of the formula

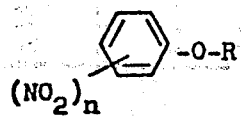

where $n$ denotes one of the integers 1 and 2 and R denotes the radical

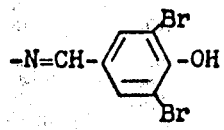

have a herbicidal action superior to that of their individual components.

Active ingredients a and b may be applied in amounts of 0.5 to 5 kg per hectare.

The weight ratio of $a:b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be applied to the loci of the plants, pre- and/or postemergence.

The agents according to the invention may be used as solution emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons, such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils. The new compounds may be mixed with fertilizers, insecticides, fungicides and other herbicides.

EXAMPLE 1

The plants wheat (*Triticum aestivum*), barley (*Hordeum vulgare*), wild oats (*Avena fatua*), slender foxtail (*Alopecurus myosuroides*), catchweed (*Galium aparine*), chickweed (*Stellaria media*) and henbit (*Lamium amplexicaule*) were treated at a growth height of 4 to 20 cm with the following amounts of the following individual active ingredients and compositions thereof, each active ingredient and each composition being emulsified or dispersed in 500 liters of water per hectare:

| | | |
|---|---|---|
| I | 4-chlorobutyn-2-yl-1 N-3-chlorophenylcarbamate, | 1 and 2 kg per hectare; |
| II | 5-chloro-4-methyl-2-propionamide thiazole, | 2 and 3 kg per hectare; |
| III | 3,5-dibromo-4-hydroxybenzaldoxime-O-(2',4'-dinitrophenyl)-ether, | 0.75 and 1.5 kg per hectare; |
| IV | 9-hydroxyfluorenecarboxylic acid-(9), | 1 and 3 kg per hectare; |
| V | 3-isopropyl-2,1,3-benzothiadiazinone-(4)-2,2-dioxide, | 0.75, 1.5, 2 and 3 kg per hectare; |
| I + V | 1.0 + 1.0 kg per hectare; | |
| II + V | 2.0 + 1.0 kg per hectare; | |
| III + V | 0.75 + 0.75 kg per hectare; | |
| IV + V | 1.0 + 2.0 kg per hectare. | |

After 8 to 12 days it was ascertained that the compositions had a better overall action than the individual active ingredients, combined with good crop plant compatibility. The results are given below:

| Active ingredient kg/ha | I 1 | I 2 | II 2 | II 3 | III 0.75 | III 1.5 | IV 1 | IV 3 | 0.75 | V 1 | V 1.5 | V 2 | V 3 | I+V 1+1 | II+V 2+1 | III+V 0.75+0.75 |
|---|---|---|---|---|---|---|---|---|---|---|---|---|---|---|---|---|
| Triticum aestivum | 0 | 0 | 10 | 20 | 0 | 10 | 0 | 0 | 0 | 0 | 0 | 0 | 0 | 0 | 10 | 0 |
| Hordeum vulgare | 0 | 0 | 10 | 20 | 5 | 15 | 0 | 15 | 0 | 0 | 0 | 0 | 0 | 0 | 10 | 0 |
| Avena fatua | 70 | 90 | 50 | 70 | — | — | — | — | 5 | 5 | 5 | 5 | 10 | 85 | 80 | — |
| Alopecuris myosuroides | 60 | 85 | 50 | 75 | — | — | — | — | 5 | 5 | 10 | 10 | 15 | 80 | 80 | — |
| Galium aparine | 5 | 10 | 30 | 45 | 20 | 45 | 30 | 85 | 35 | 40 | 60 | 70 | 80 | 80 | 90 | 90 |
| Stellaria media | 10 | 30 | 40 | 65 | 30 | 70 | 30 | 90 | 40 | 60 | 70 | 90 | 90 | 90 | 100 | 100 |
| Lamium amplexicaule | 5 | 10 | 5 | 10 | 45 | 80 | 30 | 95 | 30 | 40 | 50 | 60 | 70 | 75 | 75 | 100 |

0 = no damage
100 = complete destruction

EXAMPLE 2

In the open, various plants were treated at a growth height of 3 to 25 cm with the following amounts of the following active ingredients and compositions thereof as oil dispersions:

I    sodium salt of 3-isopropyl-2,1,3-benzothiadiazinone-4)-2,2-dioxide, 0.15, 0.45, 0.75 and 0.9 kg/hectare;

II   dimethylamine salt of 3-isopropyl-2,1,3-benzothiadiazinone-(4)-dioxide, 0.15, 0.45, 0.75 and 0.9 kg/hectare;

III  diethanolamine salt of 3-isopropyl-2,1,3-benzothiadiazinone-(4)-2,2-dioxide, 0.15, 0.45, 0.75 and 0.9 kg/hectare;

IV   3,5-dibromo-4-hydroxybenzaldoxim-0-(2',4'-dinitrophenyl)-ether, 0.15, 0.45, 0.75 and 0.9 kg/hectare;

V    3,5-diiodo-4-hydroxybenzonitrile, 0.15, 0.45, 0.75 and 0.9 kg/hectare;

VI   3,5-dibromo-4-hydroxybenzonitrile, 0.15, 0.45, 0.75 and 0.9 kg/hectare;

| | | | |
|---|---|---|---|
| I + IV: | 0.15 + 0.75; | 0.75 + 0.15; | 0.45 + 0.45 kg/ha; |
| I + V: | 0.15 + 0.75; | 0.75 + 0.15; | 0.45 + 0.45 kg/ha; |
| I + VI: | 0.15 + 0.75; | 0.75 + 0.15; | 0.45 + 0.45 kg/ha; |
| II + IV: | 0.15 + 0.75; | 0.75 + 0.15; | 0.45 + 0.45 kg/ha; |
| II + V: | 0.15 + 0.75; | 0.75 + 0.15; | 0.45 + 0.45 kg/ha; |
| II + VI: | 0.15 + 0.75; | 0.75 + 0.15; | 0.45 + 0.45 kg/ha; |
| III + IV: | 0.15 + 0.75; | 0.75 + 0.15; | 0.45 + 0.45 kg/ha; |
| III + V: | 0.15 + 0.75; | 0.75 + 0.15; | 0.45 + 0.45 kg/ha; |
| III + VI: | 0.15 + 0.75; | 0.75 + 0.15; | 0.45 + 0.45 kg/ha. |

After 8 to 12 days it was ascertained that the compositions had a better herbicidal action than their individual components, combined with the same good crop plant compatibility.

The results are given below:

| Active ingredient kg/ha | I 0.15 | I 0.45 | I 0.75 | I 0.9 | II 0.15 | II 0.45 | II 0.75 | II 0.9 | III 0.15 | III 0.45 | III 0.75 | III 0.9 |
|---|---|---|---|---|---|---|---|---|---|---|---|---|
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Galium aparine | 10 | 30 | 40 | 55 | 10 | 26 | 40 | 47 | 14 | 28 | 45 | 60 |
| Lamium amplexicaule | 0 | 10 | 15 | 23 | 0 | 9 | 20 | 35 | 3 | 10 | 25 | 32 |
| Stellaria media | 7 | 18 | 30 | 42 | 10 | 26 | 35 | 45 | 6 | 20 | 40 | 50 |
| | IV | | | | V | | | | VI | | | |
| Crop plants: | | | | | | | | | | | | |
| Triticum aestivum | 0 | 0 | 0 | 0 | 0 | 10 | 12 | 15 | 0 | 5 | 5 | 10 |
| Hordeum vulgare | 0 | 0 | 5 | 5 | 0 | 5 | 7 | 10 | 0 | 0 | 0 | 5 |
| Secale cereale | 0 | 0 | 0 | 5 | 0 | 6 | 10 | 15 | 0 | 0 | 0 | 7 |
| Unwanted plants: | | | | | | | | | | | | |
| Galium aparine | 5 | 15 | 20 | 30 | 14 | 35 | 54 | 74 | 11 | 20 | 30 | 48 |
| Lamium amplexicaule | 12 | 33 | 45 | 60 | 10 | 30 | 43 | 67 | 8 | 30 | 40 | 60 |
| Stellaria media | 7 | 22 | 30 | 48 | 10 | 25 | 37 | 58 | 7 | 20 | 31 | 50 |

| Active ingredient kg/ha | I + IV 0.15+0.75 | I + IV 0.75+0.15 | I + IV 0.45+0.45 | I + V 0.15+0.75 | I + V 0.75+0.15 | I + V 0.45+0.45 |
|---|---|---|---|---|---|---|
| Crop plants: | | | | | | |
| Triticum aestivum | 0 | 0 | 0 | 12 | 0 | 0 |
| Hordeum vulgare | 5 | 0 | 0 | 7 | 0 | 5 |
| Secale cereale | 0 | 0 | 0 | 10 | 0 | 6 |
| Unwanted plants: | | | | | | |
| Galium aparine | 70 | 80 | 83 | 96 | 90 | 88 |
| Lamium amplexicaule | 90 | 68 | 80 | 78 | 65 | 82 |
| Stellaria media | 75 | 78 | 85 | 80 | 77 | 81 |
| | I + VI | | | II + IV | | |
| Crop plants: | | | | 40 | | |
| Triticum aestivum | 5 | 0 | 5 | 0 | 0 | 0 |
| Hordeum vulgare | 0 | 0 | 0 | 5 | 0 | 0 |
| Secale cereale | 0 | 0 | 0 | | | |
| Unwanted plants: | | | | | | |
| Galium aparine | 76 | 90 | 87 | 68 | 82 | 80 |
| Lamium amplexicaule | 73 | 60 | 76 | 82 | 70 | 78 |
| Stellaria media | 75 | 73 | 80 | 80 | 79 | 90 |

| Active ingredient kg/ha | II + V 0.15+0.75 | 0.75+0.15 | 0.45+0.45 | II + VI 0.15+0.75 | 0.75+0.15 | 0.45+0.45 |
|---|---|---|---|---|---|---|
| Crop plants: | | | | | | |
| Triticum aestivum | 12 | 0 | 10 | 5 | 0 | 5 |
| Hordeum vulgare | 7 | 0 | 5 | 0 | 0 | 0 |
| Secale cereale | 10 | 0 | 6 | 0 | 0 | 0 |
| Unwanted plants: | | | | | | |
| Galium aparine | 97 | 95 | 93 | 78 | 90 | 84 |
| Lamium amplexicaule | 80 | 67 | 75 | 74 | 66 | 73 |
| Stellaria media | 85 | 83 | 92 | 80 | 85 | 88 |
| | | III + IV | | | III + V | |
| Crop plants: | | | | | | |
| Triticum aestivum | 0 | 0 | 0 | 12 | 0 | 10 |
| Hordeum vulgare | 5 | 0 | 0 | 7 | 0 | 5 |
| Secale cereale | 0 | 0 | 0 | 10 | 0 | 6 |
| Unwanted plants: | | | | | | |
| Galium aparine | 67 | 83 | 80 | 100 | 97 | 95 |
| Lamium amplexicaule | 80 | 64 | 78 | 83 | 76 | 77 |
| Stellaria media | 74 | 76 | 82 | 80 | 93 | 84 |

| Active ingredient kg/ha | III + VI 0.15+0.75 | 0.75+0.15 | 0.45+0.45 |
|---|---|---|---|
| Crop plants: | | | |
| Triticum aestivum | 5 | 0 | 5 |
| Hordeum vulgare | 0 | 0 | 0 |
| Secale cereale | 0 | 0 | 0 |
| Unwanted plants: | | | |
| Galium aparine | 80 | 92 | 86 |
| Lamium amplexicaule | 75 | 70 | 78 |
| Stellaria media | 72 | 85 | 79 |

C = no damage
100 = complete destruction

EXAMPLE 3

In the greenhouse, various plants were treated at a growth height of 4 to 27 cm with the following amounts of the following individual active ingredients and compositions thereof as dispersions:

I 3-isopropyl-2,1,3-benzothiadiazinone-(4)-2,2-dioxide, 1.0, 1.5, 2.0 and 3.0 kg/ha;

II 3,5-dibromo-4-hydroxybenzonitrile, 1.0, 1.5, 2.0 and 3.0 kg/ha;

III 3,5-diiodo-4-hydroxybenzonitrile, 1.0, 1.5, 2.0 and 3.0 kg/ha;

IV 3,5-dibromo-4-hydroxybenzaldoxime-0-(2',4'-dinitrophenyl)-ether, 1.0, 1.5, 2.0 and 3.0 kg/ha;

I + II : 2.0 + 1.0; 1.0 + 2.0; 1.0 + 1.0; and 1.5 + 1.5 kg/ha;
I + III: 2.0 + 1.0; 1.0 + 2.0; 1.0 + 1.0; and 1.5 + 1.5 kg/ha;
I + IV : 2.0 + 1.0; 1.0 + 2.0; 1.0 + 1.0; and 1.5 + 1.5 kg/ha;

compared with

V 1-p-chlorophenyl-3,3-dimethylurea, 2.0 and 3.0 kg/ha; and V+I: 2.0 + 1.0 kg/ha.

After 12 to 15 days it was ascertained that the compositions I + II, I + III and I + IV had a better crop plant compatibility than their individual components; active ingredients V; and composition V+I, combined with the same good herbicidal action.

The results are given below:

| Active ingredient kg/ha | I 1.0 | 1.5 | 2.0 | 3.0 | II 1.0 | 1.5 | 2.0 | 3.0 | III 1.0 | 1.5 | 2.0 | 3.0 |
|---|---|---|---|---|---|---|---|---|---|---|---|---|
| Crop plants: | | | | | | | | | | | | |
| Triticum aestivum | 0 | 0 | 0 | 0 | 10 | 12 | 15 | 20 | 15 | 18 | 20 | 30 |
| Hordeum vulgare | 0 | 0 | 0 | 0 | 5 | 6 | 8 | 10 | 10 | 15 | 18 | 26 |
| Secale cereale | 0 | 0 | 0 | 0 | 8 | 10 | 14 | 18 | 17 | 20 | 25 | 31 |
| Unwanted plants: | | | | | | | | | | | | |
| Galium aparine | 40 | 60 | 70 | 80 | 50 | 67 | 90 | 100 | 75 | 90 | 98 | 100 |
| Lamium amplexicaule | 40 | 50 | 60 | 70 | 60 | 70 | 85 | 100 | 70 | 80 | 94 | 100 |
| Stellaria media | 60 | 70 | 90 | 95 | 54 | 78 | 90 | 100 | 60 | 83 | 97 | 100 |

0 = no damage
100 = complete destruction

| Active ingredient kg/ha | I + II 2.0+1.0 | 1.0+2.0 | 1.0+1.0 | 1.5+1.5 | I + III 2.0+1.0 | 1.0+2.0 | 1.0+1.0 | 1.5+1.5 |
|---|---|---|---|---|---|---|---|---|
| Crop plants: | | | | | | | | |
| Triticum aestivum | 10 | 15 | 10 | 12 | 15 | 20 | 15 | 18 |
| Hordeum vulgare | 5 | 8 | 5 | 6 | 10 | 18 | 10 | 15 |
| Secale cereale | 8 | 14 | 8 | 10 | 17 | 25 | 17 | 20 |
| Unwanted plants: | | | | | | | | |
| Galium aparine | 100 | 100 | 100 | 100 | 100 | 100 | 100 | 100 |
| Lamium amplexicaule | 100 | 100 | 100 | 100 | 100 | 100 | 100 | 100 |
| Stellaria media | 100 | 100 | 100 | 100 | 100 | 100 | 100 | 100 |

9 = no damage
100 = complete destruction

| Active ingredient kg/ha | IV | | | | V | |
|---|---|---|---|---|---|---|
| | 1.0 | 1.5 | 2.0 | 3.0 | 2.0 | 3.0 |
| Crop plants: | | | | | | |
| Triticum aestivum | 0 | 10 | 15 | 19 | 40 | 70 |
| Hordeum vulgare | 7 | 15 | 20 | 25 | 47 | 80 |
| Secale cereale | 6 | 10 | 12 | 18 | 56 | 95 |
| Unwanted plants: | | | | | | |
| Galium aparine | 30 | 45 | 60 | 100 | 90 | 95 |
| Lamium amplexicaule | 65 | 80 | 95 | 100 | 100 | 100 |
| Stellaria media | 60 | 70 | 93 | 100 | 100 | 100 |

0 = no damage
100 = complete destruction

| Active ingredient kg/ha | I + IV | | | | I + V |
|---|---|---|---|---|---|
| | 2.0+1.0 | 1.0+2.0 | 1.0+1.0 | 1.5+1.5 | 1.0+2.0 |
| Crop plants: | | | | | |
| Triticum aestivum | 0 | 15 | 0 | 10 | 40 |
| Hordeum vulgare | 7 | 20 | 7 | 15 | 47 |
| Secale cereale | 6 | 12 | 6 | 10 | 56 |
| Unwanted plants: | | | | | |
| Galium aparine | 100 | 100 | 100 | 100 | 100 |
| Lamium amplexicaule | 100 | 100 | 100 | 100 | 100 |
| Stellaria media | 100 | 100 | 100 | 100 | 100 |

0 = no damage
100 = complete destruction

It is claimed:

1. A herbicide composition comprising an inert carrier having dispersed therein a herbicidally effective amount of a mixture consisting essentially of
   a. a compound of the formula

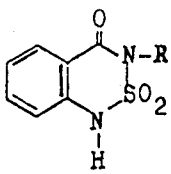

where R denotes lower alkyl of a maximum of 4 carbon atoms, or an alklai metal alkaline earth metal, ammonium, lower alkylammonium, lower hydroxyalkylammonium or hydrazine salt thereof, and
   b. a compound of the formula

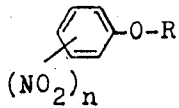

where $n$ denotes one of the integers 1 and 2, and R denotes the radical

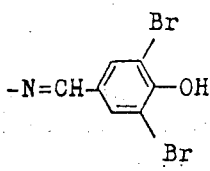

in a weight ratio of a:b of 5:1 to 1:5.

2. A herbicide composition as claimed in claim 1 wherein said weight ratio is 3:1 to 1:3 and compound (b) is 3,5-dibromo-4-hydroxybenzaldoxime-0-(2',4'-dinitrophenyl)-ether.

3. A process for controlling growth of unwanted plants which comprises applying to the loci of the plants a herbicide composition comprising an inert carrier having dispersed therein a herbicidally effective amount of a mixture consisting essentially of
   a. a compound of the formula

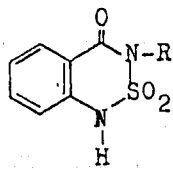

where R denotes lower alkyl of a maximum of 4 carbon atoms, or an alkali metal, alkaline earth metal, ammonium, lower alkylammonium, lower hydroxyalkylammonium or hydrazine salt thereof and
   b. a compound of the formula

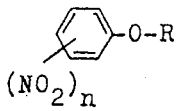

wherein $n$ denotes one of the integers 1 and 2, and R denotes the radical

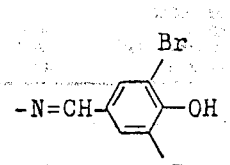

in a weight ratio of a:b of 5:1 to 1:5.

4. A process as claimed in claim 3 wherein said weight ratio is 3:1 to 1:3 and compound (b) is 3,5- dibromo-4-hydroxybenzaldoxime-0-(2',4'-dinitrophenyl)-ether.

5. A process as claimed in claim 3 wherein said weight ratio is 3:1 to 1:3, compound (b) is 3,5-dibromo-4-hydroxybenzaldoxime-0-(2',4'-dinitrophenyl)-ether, and compound a is 3-isopropyl-2,1,3-benzothiadiazinone-(4)-2,2-dioxide or said salt thereof.

6. A process as claimed in claim 3 wherein said weight ratio is 1:1, compound (b) is 3,5-dibromo-4-hydroxybenzaldoxime-0-(2',4'-dinitrophenyl)-ether, and compound a is 3-isopropyl-2,1,3-benzothiadiazinone-(4)-2,2-dioxide.

7. A herbicide composition as claimed in claim 1 wherein said weight ratio is 3:1 to 1:3, compound (b) is 3,5-dibromo-4-hydroxybenzaldoxime-0-(2',4'-dinitrophenyl)-ether, and compound a is 3-isopropyl-2,1,3-benzothiadiazinone-(4)-2,2-dioxide or said salt thereof.

8. A herbicide composition as claimed in claim 1 wherein said weight ratio is 1:1, and compound (b) is 3,5-dibromo-4-hydroxybenzaldoxime-0-(2',4'-dinitrophenyl)-ether, and compound a is 3-isopropyl-2,1,3-benzothiadiazonine-(4)-2,2-dioxide.

* * * * *